(12) United States Patent
Jarrett et al.

(10) Patent No.: US 6,841,165 B1
(45) Date of Patent: Jan. 11, 2005

(54) INSECTICIDAL AGENTS

(75) Inventors: Paul Jarrett, Wellesbourne (GB);
James Alun Wynne Morgan, Swansea (GB); Debbie Ellis, Warwick (GB)

(73) Assignee: Horticulture Research International, Warwick (GB)

( * ) Notice: Subject to any disclaimer, the term of this patent is extended or adjusted under 35 U.S.C. 154(b) by 0 days.

(21) Appl. No.: 09/856,221

(22) PCT Filed: Nov. 18, 1999

(86) PCT No.: PCT/GB99/03846

§ 371 (c)(1),
(2), (4) Date: Aug. 20, 2001

(87) PCT Pub. No.: WO00/30453

PCT Pub. Date: Jun. 2, 2000

(30) Foreign Application Priority Data

Nov. 19, 1998 (GB) .............................. 9825418

(51) Int. Cl.$^7$ ........................ A01N 25/00; A01N 25/08; C12P 21/06; C12N 1/20; C12N 1/00
(52) U.S. Cl. ........................ 424/405; 424/409; 424/410; 424/418; 435/69.1; 435/71.1; 435/252.1; 435/252.31; 435/352.5; 435/822; 435/832
(58) Field of Search ................................. 424/405, 409, 424/410, 418; 435/69.1, 71.1, 252.1, 252.31, 252.5, 822, 832

(56) References Cited

PUBLICATIONS

International J. Systematic Bacteriology. 1993. vol. 43, pp. 864–865.*

* cited by examiner

*Primary Examiner*—Jon P. Weber
*Assistant Examiner*—Kailash C. Srivastava
(74) *Attorney, Agent, or Firm*—Dann, Dorfman, Herrell & Skillman, P.C.

(57) ABSTRACT

Disclosed are novel strains of *Xenorhabdus bovienii* deposited with NCIMB under accession numbers NCIMB 40985 and NCIMB 40986 which are a source of orally acting pesticides. Also disclosed are pesticidal agents which are (i) obtainable from a *X. bovienii* strains; (ii) have oral insecticidal activity against one or more species of insect of the order *Lepidoptera, Coleoptera* or *Homoptera*; (iii) are substantially heat stable to 50° C.; and (iv) act synergistically with *B. thuringiensis* cells as an oral insecticide. The invention further makes available nucleic acids encoding these and variant toxins, plus vectors, host cells and plants transformed with the same. Also disclosed are insecticidal polypeptides (and antibodies raised to them) and compositions, plus methods of using all of these materials for the control of pests, particularly insects.

8 Claims, 2 Drawing Sheets

SEQUENCE LISTING

<160> NUMBER OF SEQ ID NOS: 14

<210> SEQ ID NO 1
<211> LENGTH: 449
<212> TYPE: DNA
<213> ORGANISM: Xenorhabdus bovienii

<400> SEQUENCE: 1
tgtgcaggca ctcaccttat tgggcgataa ccttattttt cattggataa cgattggtca     60 gaacccgtt tagaagaagc cgccagtcaa accattcgtg atcattatca gcataaaatg    120
cggcaactgc gtcaacgcgc ggccttgccg gcgaaacgta ctgcaaattc gttaaccgct    180
ttgttccttc ctcagataaa caaaaaactg caaagttact ggcagacgtt agcacaacgc    240
ctatataact tacgtcataa tctgacaatt gatggtcagc cgttgtcatt acccatctat    300
gcgacaccag cagatccgtc cgtactgctt agtgctgccg tcaccgcctc acaaggcgga    360
ggggatttgc ctcggacagt aatgccgatg taccgttttc cgattattct ggaaaatgcc    420
aagtggggag tgacccaact gatacagtt                                       449

<210> SEQ ID NO 2
<211> LENGTH: 154
<212> TYPE: DNA
<213> ORGANISM: Xenorhabdus bovienii

<400> SEQUENCE: 2
caaaccattc gtgatcatta tcagcataaa atgcggcaac tgcgtcaacg cgcggccttg     60
ccggcgaaac gtactgcaaa ttcgttaacc gctttgttcc ttcctcagat aaacaaaaaa    120
ctgcaaagtt actggcagac gttagcacaa cgcc                                 154

```
<210> SEQ ID NO 3
<211> LENGTH: 291
<212> TYPE: DNA
<213> ORGANISM: Xenorhabdus bovienii

<400> SEQUENCE: 3
aataccttgc tcaacattac tgaacggcag gatgcagaag cactggcaga attgctgcaa    60
actcaaggca gtgaattagc tttgcagagt attaaaatgc aggcaagatg attgctgaaa   120
ttgatgctga tgaagtggcg cttaaggaaa gccgtcatgg tgcacaatct cgttttgaca   180
gcttcagtac gctgtatgac gaagatgtta actccggtga aaaacaagcg atggatctgt   240
atctctcttc atcggtattg agcaccagca gtacggccct gcatatggtg c            291

<210> SEQ ID NO 4
<211> LENGTH: 332
<212> TYPE: DNA
<213> ORGANISM: Xenorhabdus bovienii

<400> SEQUENCE: 4
gtgaagcggc agtattgcaa aaaaactatc tggaaaccca acaggcacaa actcaggcac    60
agctggcctt cctacaaagc aaattcagca atacagcgtt gtataactgg ctacgtgggc   120
gattggcggc tatttattat cagttttatg acttggctgt ttccctgtgt ttgatggctg   180
aacaaactta ccagtatgaa ttgaacgata aagctgtacg cttcattaag cccggtgcct   240
ggcatggcac ttatgctggt ttgttagcag gtgaaacctt gatgctgaat ttggcacaga   300
tggaaaaaaa ctatttggaa aaagatgaac gg                                 332

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
aaggaggtga tccagccgca                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
ggagagttag atcttggctc                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
ttcggcagtc aacgctccta                                                20

<210> SEQ ID NO 8
<211> LENGTH: 20
```

```
<212> TYPE: DNA
<213> ORGANISM: Artificial Sequence
<220> FEATURE:
<223> OTHER INFORMATION: Description of Artificial Sequence: Primer

<400> SEQUENCE: 8
agcgatgcgc tggtattgtg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
ttgtctgcgg caatacgtgt                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
ttgtctgcgg caatacgtgt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
ctgcgtcagc aacacgtatt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
tgtactgccg ccataactca                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
acgacggcca gtgaattgta                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 14
cgccaagcta tttaggtgac                                              20
```

INSECTICIDAL AGENTS

TECHNICAL FIELD

The present invention relates to agents, particularly proteinaceous agents, for controlling insects or other pests. The invention further relates to materials and methods for identifying, preparing or using such agents.

PRIOR ART

Pesticidal materials, particularly insecticidal materials, are required for many applications including crop protection and insect-mediated disease control.

There is an ongoing requirement for agents and related materials which have pesticidal activity, for instance to overcome the problem of resistance to existing pesticides, or to expand the range of pests which can be controlled or the ways in which existing agents are used. Advantageously such materials have activity when taken per os by the insect target.

It is known that certain genera of nematodes contain insect-killing bacterial symbionts and that certain of these bacterial species and strains may be sources of insecticidal agents. However only a very few insecticidal agents from such sources have been demonstrated to have activity when taken per os by the pest target. This finding is perhaps unsurprising when it is considered that in nature nematodes present in the soil seek out an insect host and puncture through the insect surface such as to effectively inject pathogenic bacteria into the insect's haemocoel. By evading the insect's immune system, and producing antibiotics, enzymes and toxins, the insect is killed. The nematodes present in the insect also multiply, acquire further bacteria and are released from the decaying carcass to find a fresh insect. Thus there appears to be no particular reason why orally acting toxins should have evolved in the bacterial symbionts. The vast majority of the literature in this field confirms this. One of the earliest papers reporting that *Xenorhabdus* kills insects upon entry and growth in the haemocoel was published in 1966 by Poinar, G. A., and Thomas. O. M. (Parasitology. 56, 385–390). Since then, numerous papers have been published confirming that *Xenorhabdus* kills insects, but only once they are able to get into the haemocoel.

Patent application WO 97/17432 (Wisconsin Alumni Research Foundation) discusses insecticidal protein toxins *Photorhabdus luminescens*. These are said to have activity when used in insect food. Patent application EP 0 823 215 (Bio Integrated Technology) also discusses insecticidal *Photorhabdus* bacteria.

Patent application WO 98/08388 (MAFF) discloses methods and materials based on an insectidal toxin from *Xenorhabdus nematophilus*. These have demonstrated oral activity, for instance against *lepidopteran* and *dipteran* pest species, and were shown to act synergistically with other insect toxins such as those from *Bacillus thuringiensis*. WO 98/50427 (Dow Agrosciences LLC and Wisconsin Alumni Research Foundation) also discusses protein toxins from various *Xenorhabdus* strains.

However, as stated above, these activities are very much believed to be the exception rather than the rule.

DISCLOSURE OF THE INVENTION

The present inventors have identified and cloned novel pesticidal agents in strains of *Xenorhabdus bovienni*. As with certain other *Xenorhabdus* and *Photorhabdus* strains, in nature this species is frequently found symbiotically associated with a nematode host. Interestingly, however, the pesticidal agents discussed herein appear to be quite distinct from those identified in the prior art. For instance preferred toxins of the present invention are orally acting with high activity against the coleopteran pest species *Phaedon cochleariae*, whereas the toxins in WO 98/08388 (MAFF) apparently had no significant activity to *Phaedon*. Additionally they show some activity to the aphid species *Myzus persicae* which was not demonstrated for the *X. nematophilus* toxin of WO 98/08388 (MAFF).

Thus the invention relates, inter alia, to methods and materials for controlling insects which are based on, or related to, the insecticidal compounds from *X. bovienii* disclosed herein.

Two particular strains of *X. bovienii* which were used by the present inventors in identifying agents of the invention. These novel strains (designated H31 and I73 herein) have been deposited (under the terms of the Budapest Treaty) at the NCIMB, 23 St Machar Drive, Aberdeen, AB24 3RY, Scotland under the accession numbers NCIMB 40985 and 40986 respectively.

Certain characteristics of the strains are as follows: rod-shaped; motile; non-bioluminescent; blue on NBTA; produce antibiotics; resistant to ampicillin; form circular colonies; convex morphology; orange pigmentation. The strains were identified as belonging to the species *X. bovienii* when compared to the *X. bovienii* type strain T228 using Restriction Analysis of the complete 16S rRNA gene and partial sequence analysis as set out in the Examples below These strains, for instance in isolated or substantially isolated forms or cultures, form one aspect of the present invention.

During the assessment of these bacteria, over 200 different strains of *Xenorhabdus* spp. were tested for activity by growing them up in liquid culture and testing them at the rate of 5 µl of broth per cm$^2$ (approximately 10$^7$ cells per cm$^2$) of leaf or diet surface using *Pieris brassicae* as the primary test insect. Of the strains tested, the vast majority (including the *X. bovienii* type strain T228) showed no insecticidal activity suggesting that the assay per se did not give rise to non-specific toxicity. Subsequent purification of the toxins from the *X. bovienii* strains H31 and I73 (which had given 100% kill of the test insect) showed them to be highly active at low concentrations.

Thus in a further aspect of the present invention there is disclosed a pesticidal agent which (i) is obtainable from a *X. bovienii* strain; (ii) has oral insecticidal activity against one or more species of insect of the order *Lepidoptera*, *Coleoptera* or *Homoptera*; (iii) is substantially heat stable to 50° C.; and (iv) acts synergistically with *B. Thuringiensis* cells as an oral insecticide.

By 'oral insecticidal activity' is meant that when a pest ingests or feeds upon the agent in question it causes a toxic effect such as reduction in feeding, reduction in growth rate, reduction in fecundity or mortality.

Preferably the agent has activity against two or more, preferably three or more different orders of insect target. Examples of *Lepidopteran* targets include *Pieris brassicae* and *Plutella xylostella*, those of *Coleoptera* include *Phaedon cochleariae*, and *Homoptera* include *Myzus persicae*.

By 'substantially heat stable to 50° C.' is meant that the agent retains some pesticidal activity when tested after heating the agent in suspension to 50° C. for 10 minutes, and preferably retains at least 50% of the untreated activity, for instance when tested in a spread-feeding assay as described below over 24 hours. The agents of the present invention may not be heat stable at 80° C. However activity was not significantly affected by cold storage at 4° C. for 2 weeks.

By 'acts synergistically with *B. thuringiensis* cells as an oral pesticide' is meant that the combination of *B. thuringiensis* cellular material and agent of the present invention is more effective than the sum of the effects of the pesticides used individually. For instance the concentration of *B. thuringiensis* cellular material necessary to give 50% mortality to *P. brassicae* larvae may be reduced significantly (e.g. between 2 and 5 fold, or more) when it is used in combination with an agent of the present invention at a concentration which causes little or no mortality when at is used alone.

The agents can be obtained, purified, or enriched (for instance using the methods discussed below) from cells and cultures of *X. bovienii* or mutants thereof. The characterising properties of the agents described can be readily utilised to purify them from, or enrich their concentration in, *X. bovienii* cells and culture medium supernatants. The oral pesticidal activity provides a convenient method of assaying the level of agent after each stage, or in each sample of eluent.

Preferred *X. bovienii* strains include *X. bovienii* strains H31 and I73. These have been used by the present inventors to identify two toxins (respectively designated H toxin and I toxin hereinafter). As discussed above, these two strains are slightly different as shown by the 16S sequence data. The toxins they produce have a similar host range profile, but when purified and analysed by SDS-PA gels the two toxins apparently contain a number of proteins which have different profiles. The greatest protein difference is that I73 has a major high molecular weight protein of greater than 200 kDa which is not observed in H31. However H31 has a major protein band of approximately 180 kDa not seen in I73.

The characteristics of these agents are consistent with a protein (or possibly a combination of proteins) with a molecular weight ranging from 15 to greater than 280 kDa, possibly around 2500 amino acids long. Methods of purifying proteins from heterogenous mixtures are well known in the art (eg. selective precipitation, proteolysis, ultrafiltration with known molecular weight cut-off filters, ion-exchange chromatography, gel filtration, etc.). A particularly useful technique in this regard is ultracentrifugation (e.g. 150,000×g for over one hour). Further methods which are know to be suitable for protein purification are disclosed in "Methods in Enzymology Vol 182—Guide to Protein Purification" Ed. M P Deutscher, Pub. Academic Press Inc. Typical protocols are also set out in "Protein Purification—principles and practice" Pub. Springer-Verlag, New York Inc (1982), and by Harris & Angal (1989) "Protein purification methods—a practical approach" Pub. O.U.P. UK, or references therein.

In addition to the characteristics determined above, the present inventors have identified PCR amplified sequences which are believed to correspond to portions of the I toxin.

These sequences are similar, but not identical, to regions of the DNA encoding the proteinaceous toxin of patent application WO 98/08388 (MAFF). The sequences (designated SEQ ID No:1, SEQ ID No:2, SEQ ID No:3 and SEQ ID No:4) are shown in the attached Figures and Annex.

In a further aspect of the present invention there is provided a nucleic acid molecule encoding a toxin of the present invention, as described above.

Agents of the present invention, or nucleic acids encoding them, may be isolated and/or purified from their natural environment, in substantially pure or homogeneous form, or free or substantially free of other materials from the bacterial strain of origin. Where used herein, the term "isolated" encompasses all of these possibilities. Equally, the agents may be wholly or partially synthetic. In particular they may be 'recombinantly' produced from nucleic acid sequences which are not found together in nature (do not run contiguously) but which have been ligated or otherwise combined artificially.

Preferably the nucleic acid encodes the H toxin or I toxin disclosed above.

In one embodiment of this aspect of the invention, there is disclosed a nucleic acid encoding the I toxin, which nucleic acid comprises the nucleotide sequence shown in any one or more of SEQ ID No:1, SEQ ID No:2, SEQ ID No:3 and SEQ ID No:4. Preferably the nucleic acid comprises two, three or all of these sequences.

Naturally nucleic acids of the present invention may include extensions at the 3' or 5' termini of these sequences, or may include changes as described below. As will be appreciated by those skilled in the art, all sequence data (including that disclosed herein) may be subject to minor inaccuracies as a result of the sequencing process. Thus parts of the authentic I toxin sequence may differ slightly from the portions described herein.

Naturally, nucleic acids which are complementary to those described herein are also encompassed by the present invention.

As discussed hereinafter, the present inventors have demonstrated that toxins of the present invention e.g. from *X. bovienii*, can be used advantageously in conjunction with *Bacillus thuringiensis*, or pesticidal materials derived therefrom (eg. delta endotoxins or other isolates).

Thus in one embodiment of the present invention, the nucleic acid encodes both the *X. bovienii* toxins (or variants thereof as described below) plus also a toxin derived from *B thuringiensis*. These may optionally be encoded as a fusion protein. Sequences for *B thuringiensis* crystal proteins are disclosed by Hofte & Whiteley (1989) Microbiological Reviews: 242–255 or references discussed therein.

In a further aspect of the present invention there are disclosed nucleic acids which are variants of the H or I toxin sequences provided. A variant nucleic acid molecule shares homology (or identity) with all or part of the sequences discussed above. Generally, variants may encode, or be used to isolate or amplify nucleic acids which encode, insecticidal toxins.

Variants of the present invention can be artificial nucleic acids, which can be prepared by the skilled person in the light of the present disclosure. Alternatively they may be novel, naturally occurring, nucleic acids, isolatable using the sequences and other information disclosed herein.

Thus a variant may be a distinctive part or fragment (however produced) corresponding to a portion of the sequence provided. The fragments may encode particular functional parts of the polypeptide or they may be used for probing for, or amplifying, sequences corresponding to H toxin and I toxin or closely related sequences. Suitable lengths of fragment, and conditions, for such processes are discussed in more detail below.

Sequence variants which occur naturally may include homologs of the H toxin and I toxin genes, for instance from other bacteria, including nematode-symbionts.

Artificial variants (derivatives) may be prepared by those skilled in the art, for instance by site directed or random mutagenesis, or by direct synthesis. Preferably the variant nucleic acid is generated either directly or indirectly (e.g. via one or more amplification or replication steps) from an original nucleic encoding the H toxin or I toxin.

The term 'variant' nucleic acid as used herein encompasses all of these possibilities. When used in the context of polypeptides or proteins it indicates the encoded expression product of the variant nucleic acid i.e. variants of the H toxin or I toxin Some of the aspects of the present invention relating to variants will now be discussed in more detail.

Homology, Degeneracy and Activity

Homology (by which is meant similarity or identity) may be as defined and determined by the TBLASTN program, of Altschul et al. (1990) *J. Mol. Biol.* 215: 403–10, which is in standard use in the art (using default settings), or, and this may be preferred, the standard program BestFit, which is part of the Wisconsin Package, Version 8, Sep. 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman.

Preferably sequence comparisons are made using FASTA and FASTP (see Pearson & Lipman, 1988. Methods in Enzymology 183: 63–98). Parameters are set, using the default matrix blosum62, as follows:

Gapopen (penalty for the first residue in a gap): –12 for proteins/–16 for DNA

Gapext (penalty for additional residues in a gap): –2for proteins/–4 for DNA

KTUP word length: 2 for proteins/6 for DNA

Homology may be at the nucleotide sequence and/or encoded amino acid sequence level. Preferably, the nucleic acid and/or amino acid sequence shares at least about 85% homology, most preferably at least about 90%, 95%, 96%, 97%, 98% or 99% homology.

Homology may be over the full-length of the relevant sequence shown herein, or may be over a part of it, preferably over a contiguous sequence of about or greater than about 20, 25, 30, 33, 40, 50, 67, 133 or more amino acids or codons, compared with the sequences described herein.

Thus a variant polypeptide in accordance with the present invention may include within an H or I toxin polypeptide sequence, per 300 amino acids, a single amino acid or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence, a variant polypeptide may include additional amino acids at the C-terminus and/or N-terminus.

Naturally, changes to the nucleic acid which make no difference to the encoded polypeptide (i.e. 'degeneratively equivalent') are included.

The activity of a variant polypeptide may be assessed by transformation into a host cell capable of expressing the nucleic acid of the invention. Methodology for such transformation is described in more detail below.

Production of Derivatives

In a further aspect of the invention there is disclosed a method of producing a derivative nucleic acid comprising the step of modifying the coding sequence of the H or I toxin polynucleotide sequence.

Changes to a sequence, to produce a derivative, may be by one or more of addition, insertion, deletion or substitution of one or more nucleotides in the nucleic acid, leading to the addition, insertion, deletion or substitution of one or more amino acids in the encoded polypeptide.

Changes may be desirable for a number of reasons, including introducing or removing the following features: restriction endonuclease sequences; codon usage; other sites which are required for post translation modification; cleavage sites in the encoded polypeptide; motifs in the encoded polypeptide for glycosylation, lipoylation etc. Leader or other targeting sequences (e.g. membrane or golgi locating sequences) may be added to the expressed protein to determine its location following expression. All of these may assist in efficiently cloning and expressing an active polypeptide in recombinant form.

Other desirable mutation may be random or site directed mutagenesis in order to alter the activity (e.g. host specificity) or stability of the encoded polypeptide.

Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. altered stability or specificity.

Other methods may include mixing or incorporating sequences from related insecticidal genes (e.g. those of WO 98/08388, MAFF). For example restriction enzyme fragments of the genes could be ligated together. An alternative strategy for modifying the toxins would employ PCR (Ho et al, 1989, Gene, 77: 51–59) or DNA shuffling (Crameri et al, 1998 Nature 391.)

Identification of Variants

In a further aspect of the present invention there is provided a method of identifying and/or cloning a nucleic acid variant from a plant which method employs the sequences of the invention described above.

In each case, if need be, clones or fragments identified in the search can be extended. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence.

Such methods use probes or primers based on the nucleic acids of the present invention (including their complementary sequences, or degenerative equivalents) as discussed above. An oligonucleotide for use in probing or PCR may be about 30 or fewer nucleotides in length (e.g. 18, 21 or 24). However, if required, probing can be done with entire restriction fragments of a gene disclosed herein which may be 100's or even 1000's of nucleotides in length.

Generally, specific primers are upwards of 14 nucleotides in length. For optimum specificity and cost effectiveness, primers of 16–24 nucleotides in length may be preferred. Those skilled in the art are well versed in the design of primers for use in processes such as PCR. It may be preferable to design primers based on sequences (e.g. runs of 20 nucleotides or so) conserved between the nucleic acids of the present invention, and those disclosed for insecticidal toxins of the prior art e.g. in patent application WO 98/08388 (MAFF).

For instance I73APT.seq shares 84% identity with positions 22,256–22,706 of the *X. nematophilus* toxin disclosed in WO 98/08388. I73BPT.seq shares 85% identity with positions 22,464–22,618. I73CPT.seq shares 88% identity with positions 21,959–22,251. I73DAPT.seq shares 85% identity with positions 21,382–21,698.

In one embodiment, a variant in accordance with the present invention is also obtainable by means of a method which includes:

(a) providing a preparation of nucleic acid, e.g. from bacteria believed to be pathogenic to insects,
(b) providing a probe as described above,
(c) contacting nucleic acid in said preparation with said probe under conditions for hybridisation of said nucleic acid molecule to any said gene or homologue in said preparation, and identifying said gene or homologue if present by its hybridisation with said probe.

Potential bacterial sources of homologs may be identified by any preferred method. For instance, entomopathogenic nematodes containing bacteria can be isolated using an insect baiting technique such as that described by Bedding & Akhurst (1975) Nematologia 21: 215–227. Bacteria from nematodes identified as being pathogenic to the insect are isolated, cultured, and used as a source of nucleic acids (e.g. by analogy with the methods used in the Examples below). Preferably *Xenorhabdus* or *Photorhabdus* species are used.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as is described hereinafter. Probing may optionally be done by means of so-called 'nucleic acid chips' (see Marshall & Hodgson (1998) Nature Biotechnology 16: 27–31, for a review).

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the methods disclosed in *Molecular Cloning: a Laboratory Manual:* 2nd edition, Sambrook et al, 1989, Cold Spring Harbor Laboratory Press, using a hybridization solution comprising: 5×SSC (wherein 'SSC'=0.15 M sodium chloride; 0.15 M sodium citrate; pH 7), 5×Denhardt's reagent, 0.5–1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m=81.5°\ C.+16.6\text{Log}\ [Na+]+0.41(\%G+C)-0.63(\%\ \text{formamide})-600/\#\text{bp in duplex}$$

As an illustration of the above formula, using [Na+]=[0.368] and 50-% formamide, with GC content of 42% and an average probe size of 200 bases, the $T_m$ is 57° C. The $T_m$ of a DNA duplex decreases by 1–1.5° C. with every is decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80–90% identical, hybridization overnight at 42° C. in 0.25M $Na_2HPO_4$, pH 7.2, 6.5% SDS, 10% (w/v) dextran sulfate and a final wash at 55° C. in 0.1×SSC, 0.1% (w/v) SDS. For detection of sequences that are greater than about 90% identical, suitable conditions include hybridization overnight at 65° C. in 0.25M $Na_2HPO_4$, pH 7.2, 6.5% (w/v) SDS, 10% dextran sulfate and a final wash at 60° C. in 0.1×SSC, 0.1% (w/v) SDS.

Binding of a probe to target nucleic acid (e.g. DNA) may be measured using any of a variety of techniques at the disposal of those skilled in the art. For instance, probes may be radioactively, chemically (e.g. with biotin) fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

Amplification of Variants

In a further embodiment, hybridisation of nucleic acid molecule to a variant may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of the toxins are employed. Using RACE PCR, only one such primer may be needed (see "PCR protocols; A Guide to Methods and Applications", Eds. Innis et al, Academic Press, New York, (1990)).

Thus a method involving use of PCR in obtaining nucleic acid according to the present invention may include:

(a) providing a preparation of nucleic acid e.g. from a bacterium,
(b) providing a pair of nucleic acid molecule primers, at least one of which is specific as described above,
(c) contacting nucleic acid in said preparation with said primers under conditions for performance of PCR,
(d) performing PCR and determining the presence or absence of an amplified PCR product. The presence of an amplified PCR product may indicate identification of a variant.

In one aspect of the present invention, the nucleic acid encoding the insecticidal agent(s) described above is provided in the form of a recombinant and preferably replicable vector.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Vectors may be designed to be directly pathogenic to pests, e.g. based on an insect baculovirus (see e.g "The Baculoviruses" Ed. Lois K Miller, Pub. Plenum Press, New York and London 1997).

Specifically included are shuttle vectors by which is meant a DNA vehicle capable, naturally or by design, of replication in two different host organisms, which may be selected from actinomycetes and related species, bacteria and eucaryotic (e.g. plants, insect, mammalian, yeast or other fungal cells, including those from fruiting fungi such as mushrooms).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, yeast, filamentous fungal or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell By "promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Thus this aspect of the invention provides a gene construct, preferably a replicable vector, comprising a promoter (optionally inducible) operably linked to a nucleotide sequence provided by the present invention, such as the H or I toxin gene or a variant thereof.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, Sambrook et al (1989) supra.

Many known techniques and protocols for manipulation of nucleic acid, for example in preparation of nucleic acid constructs, mutagenesis (see above discussion in respect of variants), sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Particularly of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121–148). Suitable vectors may include plant viral-derived vectors (see e.g. EP-A-194809).

Suitable promoters which operate in plants include the Cauliflower Mosaic Virus 35S (CaMV 35S). Other examples are disclosed at pg 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177–180.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such a construct into a plant cell or a microbial cell and/or induction of expression of a construct within a plant cell, by application of a suitable stimulus e.g. an effective exogenous inducer.

In a further aspect of the invention, there is disclosed a host cell containing a heterologous construct according to the present invention, especially a plant or a microbial cell.

It may also be desirable for the host to be engineered or selected such that it also expresses other proteinaceous pesticidal materials (eg. delta-endotoxin from *B. thuringiensis*). Equally it may be desirable to generate host organisms which express fusion proteins composed of the active portion of the agent plus these other toxicity enhancing materials.

A host may be selected for the purposes of generating large quantities of pesticidal materials for purification eg. by using an expression system in *B. thuringiensis, E. coli* or a yeast or filamentous fungus. The host may be directly pathogenic to insects (e.g. an insect pathogenic fungus). The host may be a commercially important target which is predated by insects or other pests e.g. a higher plant, or mushroom. Alternatively the host may be associated with such a target (e.g. a bacterium associated with plants such as *Pseudomonas*). Preferably the host cell is a plant cell. Some of these possibilities will now be discussed in more detail.

The host cell (e.g. plant cell) is preferably transformed by the construct, which is to say that the construct becomes established within the cell, altering one or more of the cell's characteristics and hence phenotype e.g. with respect to toxicity to insects on ingestion.

Nucleic acid can be introduced into plant cells using any suitable technology, such as a disarmed Ti-plasmid vector carried by *Agrobacterium* exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4684611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

*Agrobacterium* transformation is widely used by those skilled in the art to transform dicotyledonous species. It has also been used with filamentous fungi (see de Groot et al, 1998, Nature Biotechnology 16: 839–842).

Recently, there has also been substantial progress towards the routine production of stable, fertile transgenic plants in almost all economically relevant monocot plants (see e.g. Hiei et al. (1994) *The Plant Journal* 6, 271–282)). Microprojectile bombardment, electroporation and direct DNA uptake are preferred where *Agrobacterium* alone is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention (e.g comprising the H or I toxin sequence) especially a plant or a microbial cell. In the transgenic plant cell the transgene may be on an extra-genomic vector or incorporated, preferably stably, into the genome. There may be more than one heterologous nucleotide sequence per haploid genome.

Generally speaking, following transformation, a plant may be regenerated, e.g. from single cells, callus tissue or leaf discs, as is standard in the art. Almost any plant can be entirely regenerated from cells, tissues and organs of the plant. Some techniques are reviewed in Vasil et al., *Cell Culture and Somatic Cell Genetics of Plants*, Vol I, II and III, *Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Plants which include a plant cell according to the invention are also provided.

Preferred plants of the present invention include maize, cotton, soya, rice, tomato, potato, sugar beet and *Brassica* species.

In addition to the regenerated plant, the present invention embraces all of the following: a clone of such a plant, seed, selfed or hybrid progeny and descendants (e.g. F1 and F2 descendants).

A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

The invention also provides a plant propagule from such plants, that is any part which may be used in reproduction or propagation, sexual or asexual, including cuttings, seed and so on. It also provides any part of these plants e.g. edible parts, which include the plant cells or heterologous DNA described above.

The invention further provides a method of influencing or affecting the toxicity of a plant cell, the method including causing or allowing expression of a heterologous nucleic acid sequence as discussed above within the cells of the plant.

The invention further provides a method comprising the step of causing or allowing expression of a nucleic acid encoding the H or I toxin or a variant thereof, within cells of a plant (thereby producing the encoded polypeptide)

The step may be preceded by the earlier step of introduction of the nucleic acid into a cell of the plant or an ancestor thereof.

The present invention also encompasses the expression product (generally the H or I toxin or a variant thereof) of any of the nucleic acid sequences disclosed and methods of making the expression product e.g. by expression from encoding nucleic acid therefore under suitable conditions, which may be in suitable host cells.

These products may be used in vivo (e.g. in planta).

Alternatively, following expression, the product may be isolated from the expression system (e.g. microbial) and may be used as desired, for instance in formulation of a composition including at least one additional component and/or which is adapted for oral administration.

Thus the invention further discloses oral pesticidal compositions comprising one or more agents as described above. Such compositions preferably further comprise other pesticidal materials from other *Xenorhabdus* species or non-*Xenorhabdus* species. These other materials may be chosen such as to have complementary properties to the agents described above, or act synergistically with it.

Preferably the oral pesticidal composition comprises one or more pesticidal agents as described above in combination with *B. thuringiensis* (or with a toxin derived therefrom, preferably delta endotoxin).

Further aspects of the present invention include methods of use of the *X. bovienii* strains, agents (including H or I toxins or variants thereof), compositions, nucleic acids, vectors (including modified baculoviruses), and host cells (e.g. in the form of plants) for the control of pests. Possible pest targets include mites, molluscs etc. Most preferably the target is an insect.

Preferably these materials are used to kill the insects e.g. for crop protection, by spraying crops.

Preferred insect targets of the order *Coleoptera* include *Leptinotarsa decimlineata* (Colorado beetle), *Diabrotica undecimpunctata* (Southern corn rootworm), *Diabrotica virgifera* (Western corn rootworm) and *Anthomonus grandis* (Cotton Boll Weevil).

Preferred insect targets of the order *Lepidoptera* include *Plutella xylostella* (Diamond back moth), *Heliothis virescens* (Tobacco budworm), *Pieris rapae* (Small white butterfly), *Ostrinia nubalis* (European corn borer) and *Spodoptera exigua* (Beet army worm).

In preferred forms of the invention, materials derived from *X. bovienii* (or variants) are used in conjunction with *Bacillus thuringiensis* as an oral pesticide. In further embodiments, rather than using *B. thuringiensis* itself, pesticidal materials derived from *B. thuringiensis* (eg. delta endotoxins or other isolates) are used in conjunction with *X. bovienii* species. Thus, for instance, the invention also makes available pesticidal compositions comprising cells from *X.bovienii*, in combination with *B. thuringiensis*.

Additionally, purified toxin protein, or a variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species and form a further part of the present invention.

Methods of producing antibodies include immunising a mammal (e.g. human, mouse, rat, rabbit, horse, goat, sheep or monkeys with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, *Nature* 357: 80–82). Antibodies may be polyclonal or monoclonal. As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of variant polypeptides, and then their encoding genes. Thus, the present invention provides a method of identifying or isolating an insecticidal toxin, comprising screening candidate polypeptides with a polypeptide comprising the antigen-binding domain of an antibody (for example whole antibody or a fragment thereof) which is able to bind the H or I toxins.

The invention will now be further described with reference to the following non-limiting Figures and Examples. Other embodiments of the invention will occur to those skilled in the art in the light of these.

FIGURES & SEQUENCE ANNEX

Annex I shows the sequences of the PCR products obtained in Example 7. These are (a) I73APT.SEQ; (b) I73BPT.SEQ; (c) I73CPT.SEQ and (d) I73DPT.SEQ.

EXAMPLES

Example 1

Analysis of H31 and I73 Strains of *X. bovienii*

Figure 1:
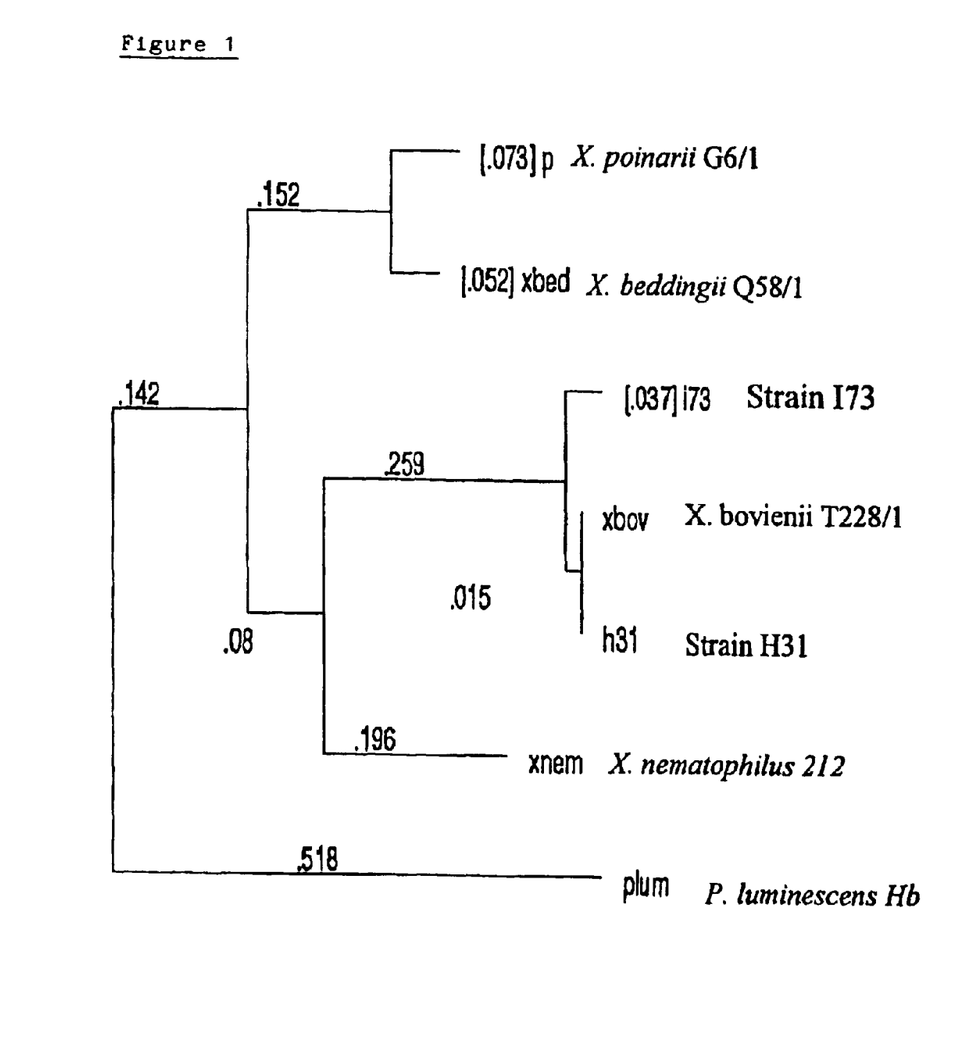
FIG. 1 shows a similarity dendogram of the RFLP pattern of the 16S rRNA gene.

These strains were identified as belonging to the species *X. bovienii* when compared to the *X. bovienii* type strain T228 using Restriction Analysis of the complete 16S rRNA gene (see Brunel et al, 1997 Applied and Environmental Microbiology: 574–580) and partial sequence analysis of these genes (FIG. 1).

PCR amplification of the 16S rRNA gene was performed on purified DNA using an omnigene thermocycler (Hybaid). DNA was isolated from bacterial cultures grown grown in 5 ml LB using the Qiagen genomic kit. To a 100 μl PCR reaction, 0.05 μl of DNA was added. The reaction mix contained 1×buffer (Flowgen), 100 pmol of each dNTP, 200 (Mol of each primer and 1 unit of Dynazyme (Flowgen). The samples were overlaid with 50 μl mineral oil. For amplification of the 16S rRNA gene the primers 'aaggaggtgatc-cagccgca' and 'ggagagttagatcttggctc' were used. Following amplification a 5 μl aliquot was run on a standard 1% (w/v) agarose gel set at 100 V for 2.5 hours to identify PCR products. The 16S rRNA gene PCR products (5–17μl) were digested with the restriction enzymes DdeI, AluI, CfoI, RsaI in a final volume of 20 μl in 1×buffer at 37° C. for 3 hours. After digestion the samples were analysed on a 2% (w/v) metaphore agarose gel (Flowgen) run at 100 V for 2.5 hours (data not shown). The presence or absence of bands of a particular size were used to generate 0/1 data for all isolates. The similarity between stains was estimated by clustal analysis of the data using GENSTAT5. A similarity dendrogram was used to display the results of this analysis (FIG. 1).

The 16S rRNA RFLP patterns of the strains H31 and I73 were similar to each other and the type strain of *X. bovienii*. Since over 4 enzymes were used to generate these patterns, the active strains were therefore identified as sub-species of *X. bovienii* (see Boemare et al, 1993 Int J Syst Bacteriol. 43: 249–255). To confirm this, partial sequence analysis of the 16S rRNA PCR products was performed. PCR products were purified using the QIAGEN PCR product clean up kit, and the quantity of DNA estimated using $A_{260}$. The primers used to amplify the 16S rRNA PCR product were used for sequencing reactions. Sequencing reactions were performed using the Applied Biosystems Big Dye Terminator cycle sequencing ready reaction kit, and analysed on an ABI automated sequencer according to manufacturers conditions. The program FASTA within the GCG Suite of DNA analysis packages was used to compare the sequence to all known sequences in the EMBL database. Greatest similarity to *X. bovienii* 16S rRNA genes was found (data not shown).

Example 2

H31 and I73 Strains of *X. bovienii* as Oral Insecticides a) Cell Growth and Preservation

*Xenorhabdus bovienii* strains H31 and I73 were each used to inoculate three, 9 cm diameter petri dishes containing L agar (10 g tryptone, 5 g Yeast Extract, 5 g NaCl and 15 g agar per Lt). Plates were incubated for 48 hrs at 26° C. and the resulting growth harvested by scraping off bacterial cells and thoroughly resuspending in 40 mls of 5% (w/v) lactose. The cells were washed once by centrifugation (5000×g for 10 mins), resuspended in 10 mls of 5% (w/v) lactose, dispensed into 1 ml aliquots and freeze dried (−60° C. for 48 hrs) for long term storage at 2° C.

b) Activity of Freeze Dried Cells i) Spread Assays

The bioassays were performed by allowing *lepidopteran* larvae to feed on diluted freeze dried cell suspensions spread over the surface of an artificial agar based diet (as described by David and Gardiner (1965) London Nature, 207, 882–883) contained in a 4.5 cm diameter plastic pot. A minimum of two pots each containing 10 larvae were used for each species. Mortalities were recorded after 6 days at 25° C.

| Insect species (instar) | Concentration $\mu$g cells/cm$^2$ | % mortality H31 | I73 |
|---|---|---|---|
| *Pieris brassicae* (1st) | 150 | 100 | 100 |
|  | 30 | 85 | 90 |
|  | 15 | 30 | 40 |
| *Plutella xylostella* (2nd) | 150 | 100 | 100 |

Thus the results show that cells from the strains are active to lepidopterous pest species ii) Leaf Disc Assays

*Phaedon cochleariae*: Second instar larvae were allowed to feed upon freeze dried cell suspensions spread over the surface of a 4.5 cm diameter Chinese cabbage leaf disc. Each disc was treated on both surfaces in duplicate with 100 $\mu$l of a 15 mg per ml cell suspension in 0.1% (v/v) Triton X-100. When cell suspensions were dry, ten second instar larvae were added per disc. Mortalities were recorded over a 6 day period at 25° C.

| Assay No. | Strain code | % mortality |
|---|---|---|
| 1. | Control | 0 |
|  | H31 | 100 |
|  | I73 | 100 |
| 2. | Control | 5 |
|  | H31 | 100 |
|  | I73 | 100 |

Thus these results clearly show that cells from *X. bovienii* strains H31 and I73 are effective as an oral insecticide against a number of insect species (and are particularly potent against *Phaedon*).

Example 3

Purification of Toxins from I73 and H31

The *Xenorhabdus bovienii* strains H31 and I73 were grown on L agar plates as in Example 2. Cells were harvested, resuspended into 40 mls of phosphate buffered saline (PBS, 0.05M PO$_4$, 0.125 M NaCl, pH 7.2) and washed once by centrifugation at 5,000×g for 10 mins. Cells were lysed by sonication on ice (18 $\mu$peak to peak for 3, 15 second periods) and the resulting lysate cleared by centrifugation at 15,000×g (average) for 15 mins at 4° C. The supernatant was retained and subjected to a high speed spin at 150,000 g for 60 mins at 4° C. The resulting pellet was re-suspended in 1 mls of PBS and stored at 4° C.

Example 4

Characterisation of Toxins from I73 and H31 a) SDS Polyacrylamide Gel Electrophoresis

Figure 2:
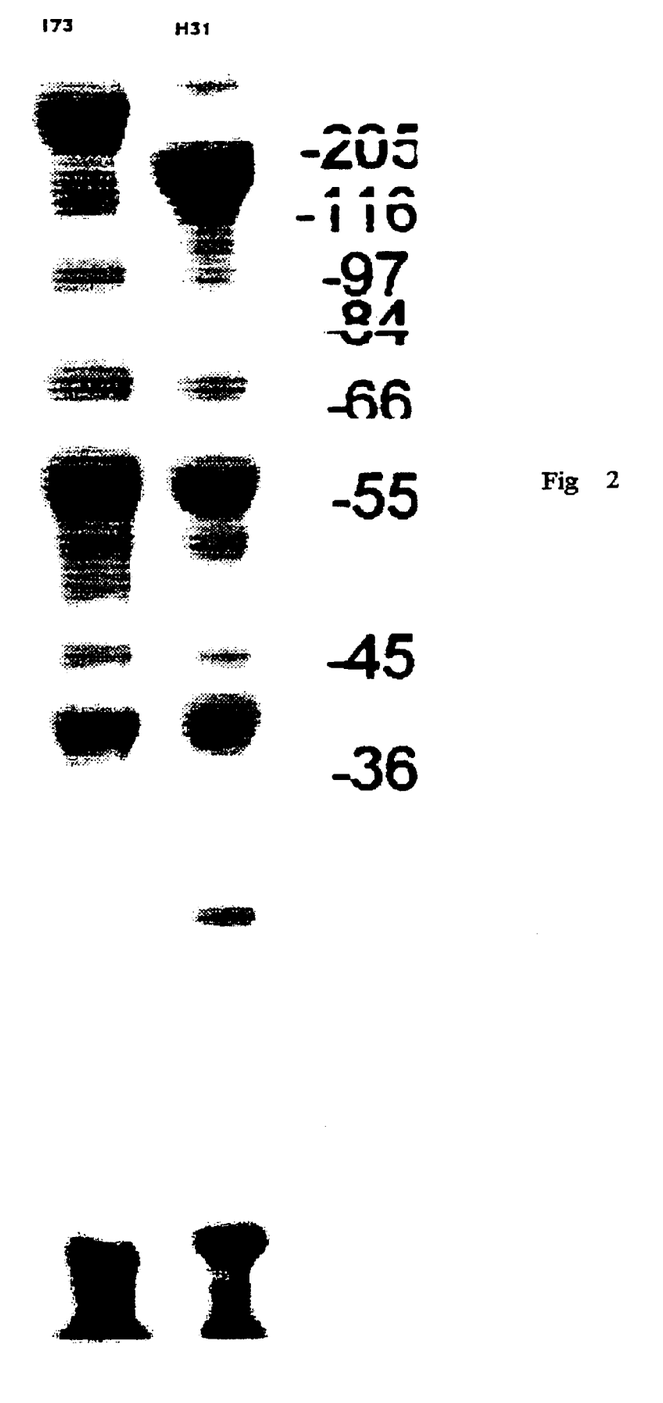
FIG. 2 shows an SDS polyacrylamide gel of purified *X. bovienii* toxins. The molecular weights of marker proteins are shown alongside.

The toxin complexes from H31 and I73 purified as described in Example 3 were analysed by SDS-PAGE using a standard apparatus and 10% polyacrylamide gels (Novagen). The gel was stained with 0.25% (w/v) Coomasie blue R250 in 40% (v/v) methanol and 10% (v/v) acetic acid. The protein masses were compared to a range of molecular weight markers standards (Sigma). The results are shown in FIG. 2.

b) Stability of Toxins from I73 and H31

Purified I73 and H31 toxins in 100 $\mu$l volumes, at a concentration of 100 $\mu$g toxin/ml were incubated for 10 minutes at 20° C, 50° C. and 80° C. Each treatment was then diluted and spread onto insect diet at 500 ng of toxin per cm$^2$, and tested for activity against *Pieris brassicae* as described in Example 2.

Results

|  | % mortality | | | |
|---|---|---|---|---|
|  | H31 | | I73 | |
| Treatment | 24 hrs | 144 hrs | 24 hrs | 144 hrs |
| 20° C. | 70 | 100 | 50 | 100 |
| 50° C. | 55 | 100 | 40 | 100 |
| 80° C. | 0 | 0 | 0 | 0 |
| no toxin | 0 | 0 | 0 | 0 |

The assay data shows that no insect activity could be detected when I73 and H31 toxins were heated at 80° C. for 10 minutes. This is the case, even though the concentration of the toxin used was at least 5 fold greater than that required to cause significant mortality. In comparison, most activity was maintained when both toxins were heated at 50° C. for 10 minutes.

Activity was not significantly affected by Triton X-100 (0.1% (v/v) for 60 mins) or cold storage at 4° C. for 2 weeks. All of these properties are consistent with a proteinaceous agent.

Example 5

Activity of Purified Toxins from I73 and H31 a) *P. brassicae* and *P. xylostella*

Initially the insecticidal activity against two *lepidopteran* species was measured using the spread assay method described in Example 2. Toxin was applied at the rate of 2 $\mu$g protein per cm$^2$ of diet.

|  | % mortality | |
|---|---|---|
| Insect species (instar) | H31 | I73 |
| *P. brassicae* (1st) | 100 | 100 |
| *P. xylostella* (2nd) | 100 | 100 |

Multi-dose assays performed against *P. brassicae* gave the following toxicity values:

| H31 | LC50 = 78.9 ng protein/cm$^2$ |
| I73 | LC50 = 232.2 ng protein/cm$^2$ |

Multi-dose bioassays performed against *P. xylostella* gave the following values:

| H31 | LC50 = 4.9 ng protein/cm$^2$ |
| I73 | LC50 = 3.5 ng protein/cm$^2$ | b) *Phaedon cochleariae*
The following values were obtained:

| Toxin | Concentration of toxin (ng/cm² of leaf) | % mortality |
|---|---|---|
| H31 | 7500 | 100 |
|  | 750 | 100 |
|  | 75 | 80 |
| I73 | 7500 | 100 |
|  | 750 | 100 |
|  | 75 | 70 |
| Control | 0 | 5 |

Multi-dose bioassays performed against *P. cochleariae* gave the following values:

| | |
|---|---|
| H31 | LC50 = 57.6 ng protein/cm² |
| I73 | LC50 = 19.4 ng protein/cm² | c) *Myzus persicae*

Activity of the purified toxins to the homopteran pest species *Myzus persicae* was tested by allowing aphids to feed on the toxin suspended in sucrose. The toxin was diluted in 15% (w/v) sucrose to a concentration of 300 μg of protein/ml and added to the inner cavity of a 1.5 ml microcentrifuge tube cap. The toxin was covered with a layer of stretched parafilm and secured onto the lid with the base of a 1.5 ml microcentrifuge tube containing 6 aphids. The aphids were incubated at 25° C. and mortalities were recorded every 24 hrs for three days.

| | 24 hours live/dead | | 48 hours live/dead | | 72 hours live/dead | |
|---|---|---|---|---|---|---|
| CONTROL (15% sucrose alone) | 24 | 0 | 23 | 1 | 18 | 6 |
| H31 | 24 | 1 | 12 | 12 | 1 | 23 |
| I73 | 20 | 4 | 9 | 16 | 0 | 24 |

Example 6
Bt Synergy of Toxins from I73 and H31
a) Production of Toxin Complex
*X. bovienii* H31 and I73 were grown and the purified toxin complex obtained as in Example 2.
b) Production of *B. thuringiensis* powder
*B. thuringiensis* strain HD 1 (available from Bacillus Genetic stock centre, The Ohio State University, Columbus, Ohio, 43210, USA) was grown up, harvested and formulated into a powder as described by Dulmage et al (1970) J. Invertebrate Pathology: 15, 15–20.
c) Activity of Toxin Complex and *B.thuringiensis* Powder Against *P brassicae*
The bioassays were carried out using the toxin complex from H31 and I73 and the *B. thuringiensis* powder in combination, or *B. thuringiensis* alone. The bioassay against neonate *P. brassicae* larvae were measured using the spread assay as in Example 2, but with various dilutions of *B. thuringiensis* in place of *X. bovienii*.
For the combination experiments, a constant dose of toxin complex at the rates of either 20 or 4 ng/cm² for H31 and 40 ng/cm² or 8 ng/cm² for I73 (which caused no mortality) were spread onto the diet. Mortality was recorded after 6 days.

d) Results

The results show that by adding either of the toxins at concentrations which when applied alone cause no insect mortality, when in combination with *B. thuringiensis* toxin (Bt) they cause a significant reduction in the concentration of Bt required to kill *Pieris brassicae* larvae. These results clearly show that combinations of the toxins (Bt and *X. bovienii*) have enhanced insecticidal activity and could be used for the improved control and resistance management of insect pests.

| Treatment | LC50 ng/cm² of insect diet |
|---|---|
| Assay1 | |
| Bt alone | 8.7 |
| Bt + 20 ng/cm² of H31 | 1.27 |
| Bt + 4 ng/cm² of H31 | 3.43 |
| Assay2 | |
| Bt alone | 8.5 |
| Bt + 40 ng/cm² of I73 | 1.42 |
| Bt + 8 ng/cm² of I73 | 2.49 |

Example 7
Sequence Analysis of Toxins from I73 and H31

Genomic DNA from strain I73 and H31 was purified (as for 16S analysis in Example 1) and the primers outlined below used to amplify DNA similar to that of the toxin gene now identified from *X. nematophilus* in WO98/08388.

| Primer pair A. | |
|---|---|
| Tox1492f | ttcggcagtcaacgctccta |
| Tox2490r | agcgatgcgctggtattgtg |
| Primer pair B. | |
| Tox5660f | ttgtctgcggcaatacgtgt |
| Tox6581r | ttgtctgcggcaatacgtgt |
| Primer pair C. | |
| Tox6551f | ctgcgtcagcaacacgtatt |
| Tox7344r | tgtactgccgccataactca |

PCR products were obtained for strain I73 with primer set B and C. Both PCR products were gel purified and cloned into the vector pGEM-T Easy (Promega). Sequences of the insert were obtained using the primers acgacggccagtgaattgta and cgccaagctatttaggtgac (designed for use with the vector).

Four areas of sequence were obtained and these are shown in Annex I at (a)–(d). From the PCR product obtained using the B primers', sequence I73APT.SEQ and I73BPT.SEQ were obtained. From the PCR product obtained using the C primers', sequences I73CPT.SEQ and I73DPT.SEQ were obtained.

The sequences are not identical to this region identified in the *X. nematophilus* toxin sequence given in WO98/08388, but as described above they are highly related (between 84%–88%). The analysis was performed using the GCG package GAP with default settings.

For H31 only a faint product for primer pair A was obtained and was not sufficient for sequencing.

| Annex I - PCR products from Example 7 |
|---|

(a) I73APT.SEQ
TGTGCAGGCACTCACCTTATTGGGCGATAACCTTATTTTTCATTGGATAACGATTGGTCA
GAACCCCGTTTAGAAGAAGCCGCCAGTCAAACCATTCGTGATCATTATCAGCATAAAATG
CGGCAACTGCGTCAACGCGCGGCCTTGCCGGCGAAACGTACTGCAAATTCGTTAACCGCT
TTGTTCCTTCCTCAGATAAACAAAAAACTGCAAAGTTACTGGCAGACGTTAGCACAACGC
CTATATAACTTACGTCATAATCTGACAATTGATGGTCAGCCGTTGTCATTACCCATCTAT
GCGACACCAGCAGATCCGTCCGTACTGCTTAGTGCTGCCGTCACCGCCTCACAAGGCGGA
GGGGATTTGCCTCGGACAGTAATGCCGATGTACCGTTTTCCGATTATTCTGGAAAATGCC
AAGTGGGGAGTGACCCAACTGATACAGTT (b) I73BPT.SEQ
CAAACCATTCGTGATCATTATCAGCATAAAATGCGGCAACTGCGTCAACGCGCGGCCTTG
CCGGCGAAACGTACTGCAAATTCGTTAACCGCTTTGTTCCTTCCTCAGATAAACAAAAAA
CTGCAAAGTTACTGGCAGACGTTAGCACAACGCC (c) I73CPT.SEQ
AATACCTTGCTCAACATTACTGAACGGCAGGATGCAGAAGCACTGGCAGAATTGCTGCAA
ACTCAAGGCAGTGAATTAGCTTTGCAGAGTATTAAAATGCAGGCAAGATGATTGCTGAAA
TTGATGCTGATGAAGTGGCGCTTAAGGAAAGCCGTCATGGTGCACAATCTCGTTTTGACA
GCTTCAGTACGCTGTATGACGAAGATGTTAACTCCGGTGAAAAACAAGCGATGGATCTGT
ATCTCTCTTCATCGGTATTGAGCACCAGCAGTACGGCCCTGCATATGGTGC (d) I73DPT.SEQ
GTGAAGCGGCAGTATTGCAAAAAAACTATCTGGAAACCCAACAGGCACAAACTCAGGCAC
AGCTGGCCTTCCTACAAAGCAAATTCAGCAATACAGCGTTGTATAACTGGCTACGTGGGC
GATTGGCGGCTATTTATTATCAGTTTTATGACTTGGCTGTTTCCCTGTGTTTGATGGCTG
AACAAACTTACCAGTATGAATTGAACGATAAAGCTGTACGCTTCATTAAGCCCGGTGCCT
GGCATGGCACTTATGCTGGTTTGTTAGCAGGTGAAACCTTGATGCTGAATTTGGCACAGA
TGGAAAAAAACTATTTGGAAAAAGATGAACGG

What is claimed is:

1. A pesticidal agent which (i) is obtained from a *Xenorhabdus bovienii* strain H31 or I73; (ii) has oral insecticidal activity against at least one species of insect of an order selected from the group consisting of *Lepidoptera, Coleoptera* and *Homoptera*; (iii) is substantially heat stable to 50° C.; and (iv) acts synergistically with *Bacillus thuringiensis* cells as an oral insecticide.

2. An agent as claimed in claimed 1 which is obtained from *Xenorhabdus bovienii* strain H31 deposited with NCIMB under accession number NCIMB 40985.

3. An agent as claimed in claim 2, wherein the agent has activity against at least one insect from two or more orders selected from the group consisting of *Lepidoptera; Coleoptera;* and *Homoptera*.

4. An agent as claimed in claim 1, which is obtained from *Xenorhabdus bovienii* strain I73 deposited with NCIMB under accession number NCIMB 40986.

5. An agent as claimed in claim 4, wherein the agent has activity against at least one insect from two or more orders selected from: *Lepidoptera; Coleoptera;* and *Homoptera*.

6. An agent as claimed in claim 4 which is a polypeptide encoded by a nucleic acid comprising a nucleotide sequence identical to any one or more of SEQ ID No:1, SEQ ID No:2, SEQ ID No:3 and SEQ ID No:4.

7. An agent as claimed in claim 1 wherein the source of said insecticidal toxin is a bacterial nematode-symbiont.

8. The pesticidal agent according to claim 1, wherein said insect species is selected from the group consisting of *Pieris brassicae, Plutella xylostella, Phaedon cochleariae* and *Myzus persicae*.

\* \* \* \* \*